US010687765B1

(12) United States Patent
Benaroya et al.

(10) Patent No.: US 10,687,765 B1
(45) Date of Patent: Jun. 23, 2020

(54) GRAPHICAL USER INTERFACE FOR PARALLEL ELECTROANATOMICAL MAPPINGS

(71) Applicant: BIOSENSE WEBSTER (ISRAEL) LTD., Yokneam (IL)

(72) Inventors: Yoav Benaroya, Kfar Saba (IL); Lidia Tonkonogi Tarasenko, Haifa (IL); Hanna Cohen-Sacomsky, Zichron Ya'acov (IL); Lilia Suzdalnitsky, Haifa (IL); Morris Ziv-Ari, Atlit (IL); Dan Sztejnberg, Hertzliya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/580,089

(22) Filed: Sep. 24, 2019

(51) Int. Cl.
*G06F 3/0482* (2013.01)
*A61B 5/00* (2006.01)
*G06F 3/0483* (2013.01)
*A61B 5/044* (2006.01)

(52) U.S. Cl.
CPC .............. *A61B 5/748* (2013.01); *A61B 5/044* (2013.01); *A61B 5/7246* (2013.01); *G06F 3/0482* (2013.01); *G06F 3/0483* (2013.01); *G06F 2203/04803* (2013.01)

(58) Field of Classification Search
CPC .......... G06F 3/00; G06F 3/048; G06F 3/0481; G06F 3/0482; G06F 3/04842; G06F 3/0483; A61B 5/00; A61B 5/0044; A61B 5/044
See application file for complete search history.

(56) References Cited

U.S. PATENT DOCUMENTS

| 10,285,611 | B1* | 5/2019 | Harlev | A61B 5/04012 |
| 2003/0236466 | A1 | 12/2003 | Tarjan | |
| 2007/0083193 | A1 | 4/2007 | Werneth | |
| 2008/0188763 | A1* | 8/2008 | John | A61B 5/0452 600/516 |
| 2012/0265084 | A1* | 10/2012 | Stewart | A61B 5/743 600/509 |
| 2013/0274623 | A1* | 10/2013 | Zhang | A61B 5/04012 600/517 |
| 2013/0281854 | A1* | 10/2013 | Stuebe | A61B 5/044 600/440 |

(Continued)

OTHER PUBLICATIONS

Carto® 3 System Instructions for Use, Biosense Webster Mar. 2019.

*Primary Examiner* — Xiomara L Bautista

(57) ABSTRACT

A system comprises a display and a processor. The processor is configured to display on the display in a graphical user interface (GUI), while a plurality of electrogram signals are acquired from a heart, a plurality of widgets corresponding to different respective electroanatomical maps generated from the electrogram signals, each of the electroanatomical maps being associated with a respective set of suitability criteria such that any one of the electrogram signals is used to generate the map only if the signal satisfies the set of suitability criteria. The processor is further configured to display in the GUI, in response to a user selecting any one of the widgets, a status of a most recently acquired one of the electrogram signals with respect to at least one criterion in the set of suitability criteria associated with the electroanatomical map to which the selected widget corresponds. Other embodiments are also described.

21 Claims, 2 Drawing Sheets

(56) References Cited

U.S. PATENT DOCUMENTS

2014/0088395 A1   3/2014   Dubois
2016/0242663 A1*  8/2016   Jayan .................. A61B 5/7275
2017/0319089 A1* 11/2017   Lou ..................... A61B 5/0472
2018/0008203 A1   1/2018   Iyun
2019/0099098 A1*  4/2019   Klebanov ............ A61B 5/7475

* cited by examiner

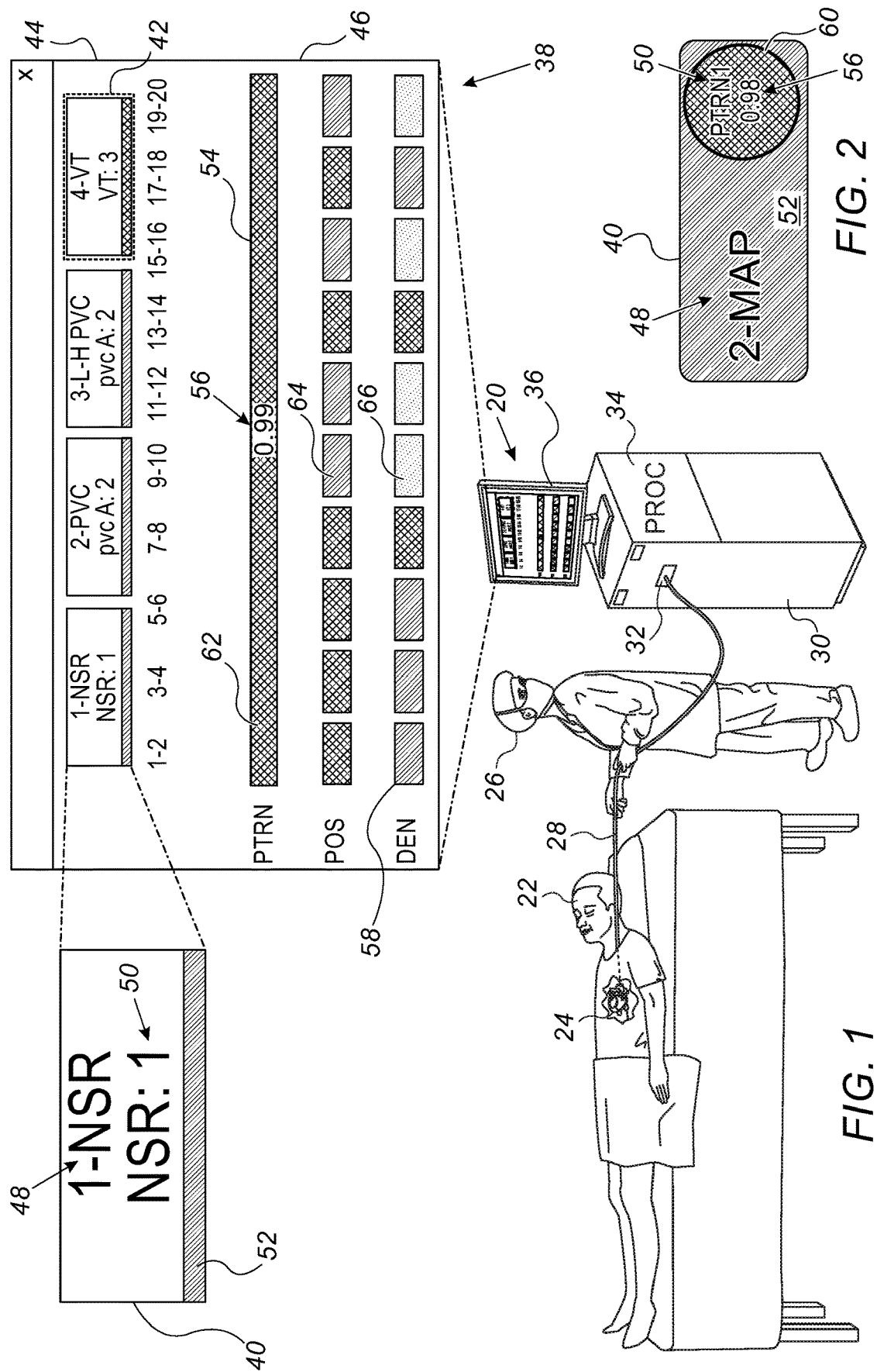

GRAPHICAL USER INTERFACE FOR PARALLEL ELECTROANATOMICAL MAPPINGS

FIELD OF THE INVENTION

The present invention relates generally to medical procedures, and particularly to electroanatomical mapping procedures.

BACKGROUND

In an electroanatomical mapping procedure, a catheter comprising one or more sensing electrodes is inserted into the heart of a patient, and the electrodes are used to acquire intracardiac electrogram signals. Based on the signals, an electroanatomical map of the heart is generated.

US Patent Application Publication 2018/0008203, whose disclosure is incorporated herein by reference, describes cardiac electrograms recorded in a plurality of channels. Beats are classified automatically into respective classifications according to a resemblance of the morphologic characteristics of the beats to members of a set of templates. Respective electroanatomic maps of the heart are generated from the classified beats.

SUMMARY OF THE INVENTION

There is provided, in accordance with some embodiments of the present invention, a system including a display and a processor. The processor is configured to display on the display in a graphical user interface (GUI), while a plurality of electrogram signals are acquired from a heart, a plurality of widgets corresponding to different respective electroanatomical maps generated from the electrogram signals, each of the electroanatomical maps being associated with a respective set of suitability criteria such that any one of the electrogram signals is used to generate the map only if the signal satisfies the set of suitability criteria. The processor is further configured to display in the GUI, in response to a user selecting any one of the widgets, a status of a most recently acquired one of the electrogram signals with respect to at least one criterion in the set of suitability criteria associated with the electroanatomical map to which the selected widget corresponds.

In some embodiments, the widgets include one or more tabs.

In some embodiments, the widgets include one or more buttons.

In some embodiments, the widgets include respective suitability indicators, and the processor is further configured to, as the electrogram signals are acquired, continually update the suitability indicator for each of the widgets to indicate whether the most recently acquired one of the electrogram signals satisfies the set of suitability criteria associated with the electroanatomical map to which the widget corresponds.

In some embodiments, the processor is configured to update the suitability indicator by changing a color of the suitability indicator.

In some embodiments, the processor is further configured to label each of the widgets with an identifier of the electroanatomical map to which the widget corresponds.

In some embodiments, the electroanatomical maps are associated with respective signal templates, in that the set of suitability criteria for each of the maps includes a criterion of matching the signal template.

In some embodiments, the processor is further configured to label each of the widgets with an identifier of the signal template with which the electroanatomical map to which the widget corresponds is associated.

In some embodiments, the widgets include respective template-matching indicators, and the processor is further configured to, as the electrogram signals are acquired, continually update the template-matching indicator for each of the widgets to indicate whether the most recently acquired one of the electrogram signals matches the template associated with the electroanatomical map to which the widget corresponds.

In some embodiments,
the processor is configured to display the widgets in a first portion of the GUI, and
the processor is configured to display the status in a second portion of the GUI while continuing to display the widgets.

There is further provided, in accordance with some embodiments of the present invention, a method that includes, while a plurality of electrogram signals are acquired from a heart, displaying, in a graphical user interface (GUI), a plurality of widgets corresponding to different respective electroanatomical maps generated from the electrogram signals, each of the electroanatomical maps being associated with a respective set of suitability criteria such that any one of the electrogram signals is used to generate the map only if the signal satisfies the set of suitability criteria. The method further includes, in response to a user selecting any one of the widgets, displaying, in the GUI, a status of a most recently acquired one of the electrogram signals with respect to at least one criterion in the set of suitability criteria associated with the electroanatomical map to which the selected widget corresponds.

There is further provided, in accordance with some embodiments of the present invention, a computer software product including a tangible non-transitory computer-readable medium in which program instructions are stored. The instructions, when read by a processor, cause the processor to display in a graphical user interface (GUI), while a plurality of electrogram signals are acquired from a heart, a plurality of widgets corresponding to different respective electroanatomical maps generated from the electrogram signals, each of the electroanatomical maps being associated with a respective set of suitability criteria such that any one of the electrogram signals is used to generate the map only if the signal satisfies the set of suitability criteria. The instructions further cause the processor to display in the GUI, in response to a user selecting any one of the widgets, a status of a most recently acquired one of the electrogram signals with respect to at least one criterion in the set of suitability criteria associated with the electroanatomical map to which the selected widget corresponds.

BRIEF DESCRIPTION OF THE DRAWINGS

The present invention will be more fully understood from the following detailed description of embodiments thereof, taken together with the drawings, in which:

FIG. 1 is a schematic illustration of a system for real time tracking of a parallel electroanatomical mapping procedure, in accordance with some embodiments of the present invention;

FIG. 2 is a schematic illustration of a widget, in accordance with some embodiments of the present invention;

DETAILED DESCRIPTION OF EMBODIMENTS

Overview

Figure 3A:
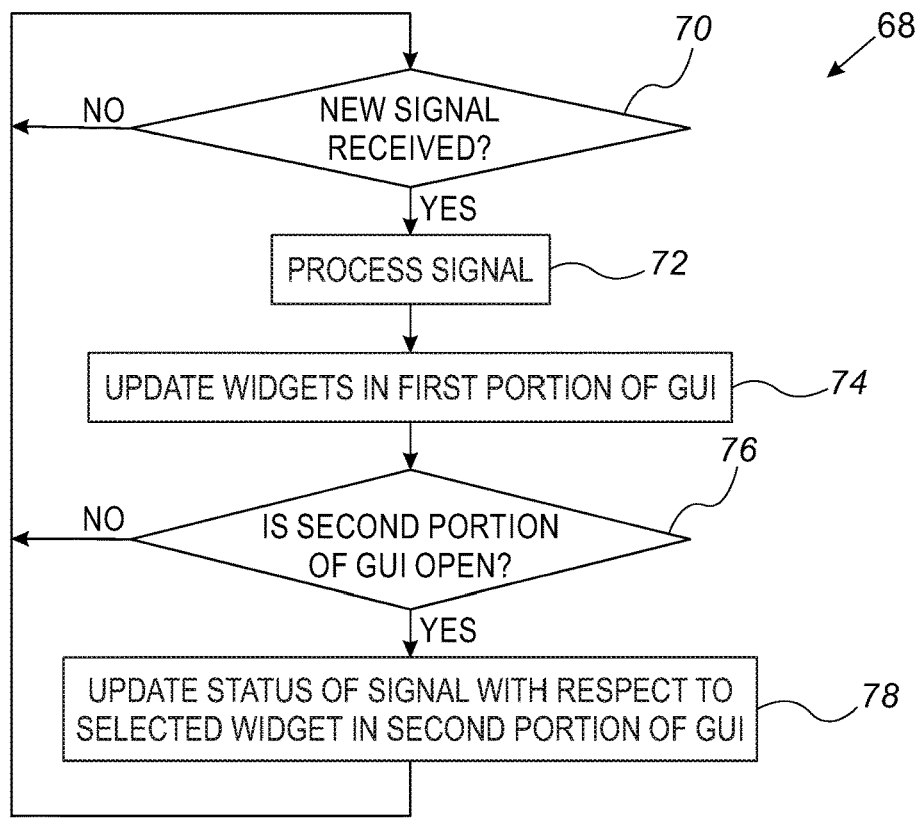
FIG. 3A is a flow diagram for a first GUI-display algorithm, in accordance with some embodiments of the present invention.

In some applications, as described in US Patent Application Publication 2018/0008203, multiple different electroanatomical maps of the heart are generated in parallel, i.e., are generated from a single session of electrogram-signal acquisition. The electroanatomical maps may correspond, for example, to different respective arrhythmic states exhibited by the patient during the session. Alternatively or additionally, the electroanatomical maps may show different types of information, or may be generated from different sets of electrogram signals.

In such applications, the maps are assigned respective sets of suitability criteria, and each acquired signal is used for a particular map only if the signal satisfies the suitability criteria for the map. The suitability criteria may include, for example, the criterion that a correlation score between the signal and a predefined signal template exceeds a predefined threshold. Alternatively or additionally, the suitability criteria may include criteria relating to the properties of the cardiac cycle over which the signal was acquired, or to the stability of the catheter while the signal was acquired.

A challenge, when performing parallel mapping as described above, is that it may be difficult for the physician to track the progression of the mapping procedure in real time, due to the multiplicity of the maps.

To address this challenge, embodiments of the present invention provide a graphical user interface (GUI) for parallel mapping. The GUI includes a plurality of widgets, such as buttons or tabs, which are typically arranged in a row or column. Each widget corresponds to a different respective one of the maps. Upon the physician selecting any one of the widgets, the GUI displays the status of the most-recently acquired electrogram signal with respect to the suitability criteria for the corresponding map. For example, the GUI may show the correlation score between the signal and the signal template, along with an indication as to whether the score exceeds the relevant threshold.

Advantageously, each widget may indicate whether the signal satisfies the suitability criteria, such that the physician may readily ascertain this information even without selecting the widget. Alternatively or additionally, the widget may include other high-level information, such as the aforementioned correlation score. Alternatively or additionally, the widget may include the name of the map and/or the name of the signal template used for the map.

System Description

Reference is initially made to FIG. 1, which is a schematic illustration of a system 20 for real time tracking of a parallel electroanatomical mapping procedure, in accordance with some embodiments of the present invention.

FIG. 1 depicts a physician 26 performing a parallel electroanatomical mapping of a chamber of the heart 24 of a patient 22. To perform the mapping, physician 26 inserts a catheter 28 into the chamber. Subsequently, the physician uses one or more electrodes disposed at the distal end of catheter 28 (which may be referred to as a "probe") to acquire electrogram signals from the chamber.

Typically, one electrogram signal is acquired during each cycle of heart 24. In some cases, each acquired signal is a single-channel signal. For example, the signal may represent the voltage between a single electrode at the distal end of catheter and an external electrode disposed on the patient's body. Alternatively, the signal may represent the voltage between a pair of electrodes at the distal end of the catheter. In other cases, each acquired signal is a multichannel signal. For example, the distal end of the catheter may comprise multiple pairs of electrodes, and each pair may acquire a respective channel of the signal.

System 20 comprises a processor 34. As the electrogram signals are acquired, processor 34 receives the signals from catheter 28. For example, the processor may be disposed within a console 30, and the proximal end of the catheter may be connected to console 30 via an electrical interface 32 such as a port or socket, such that each acquired signal passes through the catheter and, via interface 32, into the console. After passing through analog-to-digital conversion circuitry and any other relevant circuitry, each signal may be received by processor 34.

Based on the received electrogram signals, the processor generates multiple electroanatomical maps. Each electroanatomical map is associated with a respective set of suitability criteria such that any particular electrogram signal is used to generate the map only if the signal satisfies the set of suitability criteria. For example, the electroanatomical maps may be associated with respective signal templates, in that the set of suitability criteria for each of the maps may include a criterion of matching the signal template. In other words, any particular electrogram signal may be used to generate the map only if the signal matches the signal template.

In some embodiments, the electroanatomical maps are generated in stages. For example, each electroanatomical map may be initialized, prior to the procedure, from a pre-acquired anatomical map of the chamber. Subsequently to the initialization of the map, the map may be continually updated as the electrogram signals are acquired. Alternatively, each map may be initialized during the procedure based on both electrical and anatomical information acquired during the procedure, and then continually updated as further electrogram signals are acquired. In other embodiments, the electroanatomical maps are generated in a single step, following the acquisition of all the electrogram signals.

System further comprises a display 36, which may comprise, for example, a desktop or laptop computer monitor. Processor 34 may display one or more of the electroanatomical maps on display 36, during and/or subsequently to the mapping procedure. Furthermore, as the signals are acquired, processor 34 displays a graphical user interface (GUI) 38 on display 36. GUI 38 includes a plurality of widgets 40, including one or more tabs and/or one or more buttons, corresponding to the electroanatomical maps. Typically, widgets 40 are arranged in a row or column.

System 20 further comprises one or more input devices, such as a keyboard or mouse. Alternatively or additionally, display 36 may function as an input device, in that the display may comprise a touch screen. Using any of these input devices, a user of the system, such as physician 26, may select any one of widgets 40. For example, the user may hover a mouse pointer over the widget and then click a mouse button, or, if the display comprises a touch screen, simply touch the screen at the location of the widget.

In some embodiments, the processor labels each widget with an identifier 48 of the electroanatomical map to which the widget corresponds. Alternatively or additionally, the processor may label each widget with an identifier 50 of the signal template with which the corresponding electroanatomical map is associated. Each of identifiers 48 and 50 may include any suitable sequence of letters, numbers, and/or other characters, which may be entered by the user (or by another user) at any time prior to the procedure, e.g., using a keyboard. For example, in FIG. 1, the leftmost widget has two labels: "1-NSR," which indicates the first map by its number ("1") and name ("NSR"), and "NSR: 1," which likewise indicates the template associated with the first map by its number ("1") and name ("NSR").

In response to the user selecting any one of widgets 40, the processor displays, in the GUI, the status of the most recently acquired electrogram signal with respect to at least one criterion (e.g., each criterion) in the set of suitability criteria associated with the electroanatomical map to which the selected widget corresponds. Typically, the processor displays the status while continuing to display the widgets. For example, the widgets may be displayed in a first portion 44 of the GUI, while the status of the most recently acquired electrogram signal may be displayed in a second portion 46 of the GUI, which may be located, for example, beneath first portion 44. In some embodiments, particularly if the widgets are not tabs, the processor modifies the appearance of the selected widget, e.g., by displaying a border 42 around the widget, to indicate that the widget was selected.

For example, FIG. 1 shows a scenario in which the user has selected the fourth, rightmost widget. Responsively to this selection, the processor displays the status of the most recently acquired electrogram signal with respect to the set of suitability criteria associated with the fourth map.

Typically, the processor displays the status of the most recently acquired electrogram signal by displaying a plurality of indicators, each indicator indicating whether the signal satisfies a different respective one of the criteria.

For example, the processor may display an indicator 54 indicating whether the signal matches the template (referred to as a "pattern" ("PTRN") in FIG. 1) associated with the map. The signal may be deemed to match if, for example, a correlation score 56 between the signal and the template exceeds a predefined threshold. Correlation score 56 may also be displayed in second portion 46, e.g., inside indicator 54.

Alternatively or additionally to displaying indicator 54, the processor may display, for each channel and for each channel-specific criterion, a channel-specific indicator 58 indicating whether the channel-specific criterion is satisfied by the channel. For example, in FIG. 1, a channel-specific indicator 58 is displayed for each of the channels 1-2, 3-4, . . . , 19-20 and for each of the channel-specific criteria designated as "POS" and "DEN." (Each pair of numbers in the list of channels refers to a different respective pair of electrodes.)

In some embodiments, indicator 54 includes a portion (e.g., a rectangular or circular portion) of the GUI that is colored in a first color 62 (e.g., green) if the signal matches the template, and a second color 64 (e.g., red) if the signal does not match. Similarly, each channel-specific indicator 58 may include a portion (e.g., a rectangular or circular portion) of the GUI that is colored in first color 62 if the criterion is satisfied, and second color 64 otherwise. A third color 66 (e.g., gray) may be used to indicate the absence of a channel-specific criterion, and/or to indicate no acquisition over the channel.

Typically, widgets 40 include respective suitability indicators 52. As the electrogram signals are acquired, the processor continually updates suitability indicator 52 for each of the widgets to indicate whether the most recently acquired electrogram signal satisfies the set of suitability criteria associated with the corresponding map. As described above, the signal is used to generate the map only if the signal satisfies the suitability criteria.

For example, suitability indicator 52 may include a portion of the widget whose color is continually changed by the processor. In other words, after each signal is acquired, the processor may set the color of the suitability indicator to a first color (e.g., green) if the signal satisfies the suitability criteria, and to a second color (e.g., red) otherwise. In some embodiments, as shown in FIG. 1, suitability indicator 52 includes a relatively small portion of the widget, such as a horizontal strip along the bottom of the widget. In other embodiments, suitability indicator 52 includes most or all of the widget, as shown, for example, in FIG. 2 (described below).

In general, the set of suitability criteria may specify any minimum number of channels for which the channel-specific criteria must be satisfied. For example, the signal may be deemed to satisfy the set of suitability criteria if at least one channel satisfies each of the channel-specific criteria, provided that any non-channel-specific criteria are satisfied.

In some embodiments, the processor modifies suitability indicator 52 to indicate the number of channels satisfying each of the channel-specific criteria. For example, the processor may vary the shade of suitability indicator 52 in accordance with the number of channels, such that, for example, a lighter or darker shade of green indicates a greater number of channels. Alternatively or additionally, the processor may vary the size of suitability indicator 52 in accordance with the number of channels. For example, if the suitability indicator includes a horizontal strip as shown in FIG. 1, the processor may vary the length of the horizontal strip. Alternatively or additionally, the suitability indicator may include an explicit indication of the number of channels, such that, for example, "3/10" indicates that three of ten channels satisfied each of the channel-specific criteria.

In some embodiments, the GUI may be displayed in either a fully-open mode or a partially-open mode. In the fully-open mode, both first portion 44 and second portion 46 of the GUI are displayed, as shown in FIG. 1. In the partially-open mode, only the first portion, which includes widgets 40, is displayed. Any suitable input from the user (received, for example, via a mouse or keyboard) may toggle between the two modes. Thus, for example, in response to receiving a mode-toggling input when the GUI is fully open, the processor may close second portion 46 such that only first portion 44 is displayed; conversely, when the GUI is only partially open, the processor may open second portion 46 in response to the mode-toggling input. (In some embodiments, when the GUI is initially displayed, the second portion of the GUI is closed. In other embodiments, the second portion of the GUI is initially open, and one of the widgets, such as the leftmost widget, is initially selected by default.)

In general, processor 34 may be embodied as a single processor, or as a cooperatively networked or clustered set of processors. In some embodiments, the functionality of processor 34, as described herein, is implemented solely in hardware, e.g., using one or more Application-Specific Integrated Circuits (ASICs) or Field-Programmable Gate Arrays (FPGAs). In other embodiments, the functionality of processor 34 is implemented at least partly in software. For example, in some embodiments, processor 34 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Reference is now made to FIG. 2, which is a schematic illustration of a widget 40, in accordance with some embodiments of the present invention.

In some embodiments, each widget includes a respective template-matching indicator 60. As the electrogram signals are acquired, the processor continually modifies template-matching indicator 60 for each of the widgets to indicate whether the most recently acquired signal matches the template associated with the electroanatomical map to which the widget corresponds. For example, the template-matching indicator may include a portion (e.g., a rectangular or circular portion) of the widget colored by the processor in a first color (e.g., green) if the signal matches the template, and a second color (e.g., red) if the signal does not match the template. Optionally, the processor may further display identifier 50 and/or correlation score 56 inside the template-matching indicator. (In some such embodiments, indicator 54 may be omitted from second portion 46 of the GUI.)

(It is noted that even if the signal matches the template, the signal may nonetheless not satisfy the set of suitability criteria. Hence, as shown in FIG. 2, template-matching indicator 60 may be colored differently from suitability indicator 52.)

It is emphasized that, notwithstanding the particular examples shown in FIGS. 1-2, the scope of the present invention includes any suitable design for GUI 38 and widgets 40.

Example Algorithms

Reference is now made to FIG. 3A, which is a flow diagram for a first GUI-display algorithm 68, in accordance with some embodiments of the present invention.

In first GUI-display algorithm 68, the processor continually checks, at a first checking step 70, whether a new signal was received from the catheter. Upon ascertaining that a new signal was received, the processor processes the signal at a signal-processing step 72. For example, the processor may ascertain whether each channel of the signal satisfies the relevant channel-specific criteria, and/or compute the correlation score between the signal and a predefined signal template.

Subsequently to processing the signal, the processor, at a widget-updating step 74, updates the widgets in the first portion of the GUI, based on the signal processing. For example, the processor may change the color of the suitability indicator of one or more of the widgets. (In the event that the widgets include only static information such as map names, or in the event that no updates to the widgets are required, widget-updating step 74 is not performed.)

Following widget-updating step 74, the processor checks, at a second checking step 76, whether the second portion of the GUI is open. If yes, the processor, at a status-updating step 78, updates the status of the signal with respect to the selected widget (i.e., with respect to the map to which the selected widget corresponds) in the second portion of the GUI, based on the signal processing. For example, the processor may change the color of one or more channel-specific indicators. (In the event that no updates to the status are required, status-updating step 78 is not performed.) Following status-updating step 78, or if the second portion of the GUI is closed, the processor returns to first checking step 70.

Figure 3B:
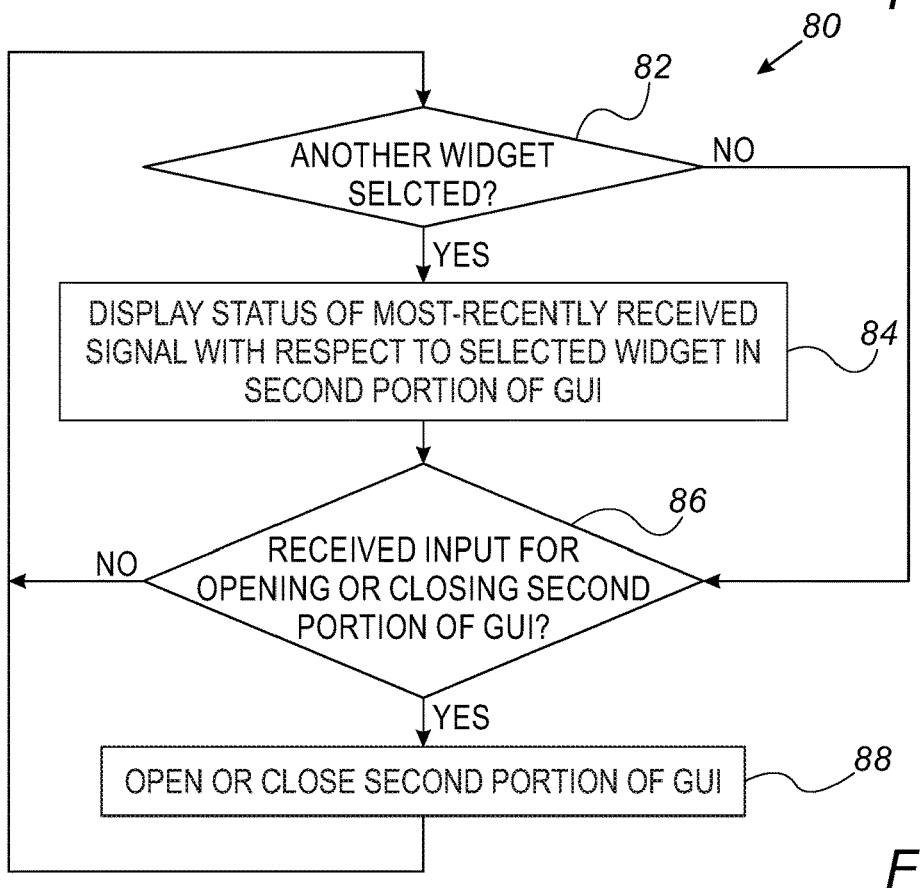
FIG. 3B is a flow diagram for a second GUI-display algorithm, in accordance with some embodiments of the present invention.

Reference is now made to FIG. 3B, which is a flow diagram for a second GUI-display algorithm 80, in accordance with some embodiments of the present invention. Typically, the processor executes second GUI-display algorithm 80 in parallel to first GUI-display algorithm 68.

In second GUI-display algorithm 80, the processor continually checks, at a third checking step 82, whether another widget, which is different from the currently-selected widget, was selected by the user. If yes, the processor, at a status-displaying step 84, displays the status of the most-recently received signal with respect to the selected widget in the second portion of the GUI. (If the second portion of the GUI was closed when the widget was selected, the processor may open the second portion of the GUI prior to performing status-displaying step 84.)

Subsequently to status-displaying step 84, or if no other widget was selected, the processor checks, at a fourth checking step 86, whether input for opening or closing the second portion of the GUI was received. If yes, the processor, at an opening-or-closing step 88, opens or closes the second portion of the GUI, in accordance with the input. Subsequently, or if no input for opening or closing the second portion of the GUI was received, the processor returns to third checking step 82.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a display; and
   a processor, configured:
   to display on the display in a graphical user interface (GUI), while a plurality of electrogram signals are acquired from a heart, a plurality of widgets corresponding to different respective electroanatomical maps generated from the electrogram signals,
   each of the electroanatomical maps being associated with a respective set of suitability criteria such that any one of the electrogram signals is used to generate the map only if the signal satisfies the set of suitability criteria, and
   to display in the GUI, in response to a user selecting any one of the widgets, a status of a most recently acquired one of the electrogram signals with respect to at least one criterion in the set of suitability criteria associated with the electroanatomical map to which the selected widget corresponds.

2. The system according to claim 1, wherein the widgets include one or more tabs.

3. The system according to claim 1, wherein the widgets include one or more buttons.

4. The system according to claim 1, wherein the widgets include respective suitability indicators, and wherein the processor is further configured to, as the electrogram signals are acquired, continually update the suitability indicator for each of the widgets to indicate whether the most recently acquired one of the electrogram signals satisfies the set of suitability criteria associated with the electroanatomical map to which the widget corresponds.

5. The system according to claim 4, wherein the processor is configured to update the suitability indicator by changing a color of the suitability indicator.

6. The system according to claim 1, wherein the processor is further configured to label each of the widgets with an identifier of the electroanatomical map to which the widget corresponds.

7. The system according to claim 1, wherein the electroanatomical maps are associated with respective signal templates, in that the set of suitability criteria for each of the maps includes a criterion of matching the signal template.

8. The system according to claim 7, wherein the processor is further configured to label each of the widgets with an identifier of the signal template with which the electroanatomical map to which the widget corresponds is associated.

9. The system according to claim 7, wherein the widgets include respective template-matching indicators, and wherein the processor is further configured to, as the electrogram signals are acquired, continually update the template-matching indicator for each of the widgets to indicate whether the most recently acquired one of the electrogram signals matches the template associated with the electroanatomical map to which the widget corresponds.

10. The system according to claim 1,
wherein the processor is configured to display the widgets in a first portion of the GUI, and
wherein the processor is configured to display the status in a second portion of the GUI while continuing to display the widgets.

11. A method, comprising:
while a plurality of electrogram signals are acquired from a heart, displaying, in a graphical user interface (GUI), a plurality of widgets corresponding to different respective electroanatomical maps generated from the electrogram signals,
each of the electroanatomical maps being associated with a respective set of suitability criteria such that any one of the electrogram signals is used to generate the map only if the signal satisfies the set of suitability criteria; and
in response to a user selecting any one of the widgets, displaying, in the GUI, a status of a most recently acquired one of the electrogram signals with respect to at least one criterion in the set of suitability criteria associated with the electroanatomical map to which the selected widget corresponds.

12. The method according to claim 11, wherein the widgets include one or more tabs.

13. The method according to claim 11, wherein the widgets include one or more buttons.

14. The method according to claim 11, wherein the widgets include respective suitability indicators, and wherein the method further comprises, as the electrogram signals are acquired, continually updating the suitability indicator for each of the widgets to indicate whether the most recently acquired one of the electrogram signals satisfies the set of suitability criteria associated with the electroanatomical map to which the widget corresponds.

15. The method according to claim 14, wherein updating the suitability indicator comprises updating the suitability indicator by changing a color of the suitability indicator.

16. The method according to claim 11, further comprising labeling each of the widgets with an identifier of the electroanatomical map to which the widget corresponds.

17. The method according to claim 11, wherein the electroanatomical maps are associated with respective signal templates, in that the set of suitability criteria for each of the maps includes a criterion of matching the signal template.

18. The method according to claim 17, further comprising labeling each of the widgets with an identifier of the signal template with which the electroanatomical map to which the widget corresponds is associated.

19. The method according to claim 17, wherein the widgets include respective template-matching indicators, and wherein the method further comprises, as the electrogram signals are acquired, continually updating the template-matching indicator for each of the widgets to indicate whether the most recently acquired one of the electrogram signals matches the template associated with the electroanatomical map to which the widget corresponds.

20. The method according to claim 11,
wherein displaying the widgets comprises displaying the widgets in a first portion of the GUI, and
wherein displaying the status comprises displaying the status in a second portion of the GUI while continuing to display the widgets.

21. A computer software product comprising a tangible non-transitory computer-readable medium in which program instructions are stored, which instructions, when read by a processor, cause the processor:
to display in a graphical user interface (GUI), while a plurality of electrogram signals are acquired from a heart, a plurality of widgets corresponding to different respective electroanatomical maps generated from the electrogram signals,
each of the electroanatomical maps being associated with a respective set of suitability criteria such that any one of the electrogram signals is used to generate the map only if the signal satisfies the set of suitability criteria, and
to display in the GUI, in response to a user selecting any one of the widgets, a status of a most recently acquired one of the electrogram signals with respect to at least one criterion in the set of suitability criteria associated with the electroanatomical map to which the selected widget corresponds.

* * * * *